United States Patent [19]

Li

[11] Patent Number: 5,001,281

[45] Date of Patent: Mar. 19, 1991

[54] ISOMERIZATION OF BIS-PHENOLS

[75] Inventor: Simon M. Li, Houston, Tex.

[73] Assignee: Shell Oil Company, Houston, Tex.

[21] Appl. No.: 392,506

[22] Filed: Aug. 11, 1989

[51] Int. Cl.$^5$ .................... C07C 31/20; C07C 39/16
[52] U.S. Cl. ............................... 568/727; 568/722; 568/723; 568/724; 568/728
[58] Field of Search ............ 568/722, 724, 727, 723, 568/728

[56] References Cited

U.S. PATENT DOCUMENTS

| 4,053,533 | 10/1977 | McClure et al. | 568/727 |
| 4,191,843 | 3/1980 | Kwates et al. | 568/728 |
| 4,375,567 | 3/1983 | Faler | 568/727 |
| 4,822,923 | 4/1989 | Li | 568/724 |
| 4,825,010 | 4/1989 | Li | 568/724 |

FOREIGN PATENT DOCUMENTS

| 0098229 | 6/1982 | Japan | 568/723 |
| 0114540 | 7/1982 | Japan | 568/722 |
| 2201833 | 9/1987 | Japan | 568/722 |

Primary Examiner—Werren B. Lone

[57] ABSTRACT

Bis-phenols are isomerized in the presence of an acidic perfluorinated polymer catalyst.

20 Claims, 1 Drawing Sheet

ISOMERIZATION OF BIS-PHENOLS

FIELD OF THE INVENTION

The present invention relates to the isomerization of a bis-phenol with an acidic perfluorinated cation exchange resin.

BACKGROUND OF THE INVENTION

Many processes are known to prepare bis-phenols. In some of these processes phenol is reacted with acetone to form bis-phenol-A. It is customary to then isolate the bis-phenol-A by crystallization, distillation or adduct crystallization. The concentrated residue contains many isomerizable components, such as o,p'-bis-phenol-A and other variations from bis-phenol-A. These components of the residue are usually isomerized in an acidic medium to the desired bis-phenol-A. The acidic medium includes inorganic acids such as hydrochloric acid and acidic cation exchange resins.

U.S. Pat. No. 3,221,061 discloses the preparation of bis-phenol-A and a subsequent "rearrangement" reaction conducted in the presence of a phenol saturated (mercapto alcohol modified) cation exchange resin.

U.S. Pat. No. 4,400,555 discloses a multi-step synthesis of bis-phenol-A in which acetone is injected in portions and an isomerization follows but the patent fails to illustrate the kind of catalyst in the isomerization zone.

U.S. Pat. No. 4,590,303 discloses a similar process in which the catalyst in the "rearrangement" reaction is a mercapto modified macroporous ion exchange resin and the acetone is injected into the "rearrangement" reactor. While the total conversion of acetone was increased, the percentage of undesired by-products also increased. However, from the data in the experiments in this patent, it can be seen that diverting a part of the acetone to the "rearrangement" reactor was adverse to isomerization since the selectivity to the desired bis-phenol-A became progressively worse. Thus, the desired isomerization was not demonstrated.

U.S. Pat. No. 4,375,567 discloses that both microreticular and macroreticular ion exchange resins in an unmodified form are used for isomerization. In this case, the microreticular resins were less effective for isomerization than the macroreticular resins.

There still exists a need to reduce or utilize the amount of undesirable by-products from the preparation of bis-phenols, e.g., bis-phenol-A from phenol and acetone or bis-phenolfluorene from phenol and 9-fluorenone. Obviously, the art has failed to find a method to react the two starting materials without the production of by-product isomers. Thus, there is still a need to more effectively convert these undesired isomers into the desired bis-phenol. The present invention addresses this problem and provides a new method to isomerize the undesired bis-phenols to the desired bis-phenol.

SUMMARY OF THE INVENTION

The present invention is directed to a process for isomerizing a bis-phenol from a phenol and a ketone, which comprises treating a bis-phenol with a catalytic amount of an acidic perfluorinated polymer to isomerize the by-products and recovering an isomerization product having a higher concentration of the desired bis-phenol, e.g., having the 4,4'-dihydroxy form.

The present invention is useful in recovering more of a desired bis-phenol, e.g., bis-phenol-A or p,p'-bis-phenolfluorene, by isomerization of an undesired bis-phenol such as 2,4'-dihydroxy-2,2-diphenyl propane (commonly referred to as o,p'-BPA) or o,p'-bisphenol fluorene and related by-products to the desired bis-phenol-A or p,p'-bis-phenolfluorene with less formation of other undesirable impurities, such as cyclic by-products and other heavy by-products and the like.

The present invention is useful for the isomerization of certain undesirable by-products from the preparation of a bis-phenol from a ketone and a phenol. The bis-phenols include those prepared by the reaction of a ketone, such as acetone, ethyl methyl ketone, isobutyl methyl ketone, acetophenone, cyclohexanone, 1,3-dichloro acetone, 9-fluorenone and the like, with a phenol, such as phenol, o-cresol, m-cresol, o-chlorophenol, m-chlorophenol, o-t-butylphenol, 2,6-xylenol, 2,5-di-t-butylphenol o-phenylphenol and the like. The above is not meant to limit the invention but to illustrate representative examples of ketones and phenols which are known in the art to make desirable bis-phenol and for which those of skill in the art can substitute other conventional bis-phenol reactants.

The catalysts for the isomerization are acidic perfluorinated polymers. Such polymers which can be used as catalysts, include those perfluorinated polymers that are prepared by conventional polymerization procedures known in the art from a perfluorinated precursor. The acidic perfluorinated polymers usually comprises a copolymer of an ethylenically unsaturated monomer, e.g., an alpha olefin, such as tetrafluoroethylene, ethylene, propylene or the like and perfluorinated monomers containing acid or precursor acid groups. The resulting copolymers can preferably contain from about 0.5 to about 50 mole percent of perfluorinated sulfonic acid groups. Suitable perfluorinated polymers include those disclosed in U.S. Pat. Nos. 4,303,551, 4,544,458, 4,626,553 incorporated by reference.

The perfluorinated polymers can be supported on a solid substrate for use in the isomerization process of the present invention. Suitable supports include metallic or inorganic solids, such as aluminum, monel, nickel, titanium, copper, brass, stainless steel (Hasteloy), tantalum, silicon carbide, glass, asbestos, zirconium, sulfonyl fluoride polymer, polyolefin, polyamide, polyester polymers, ceramic materials and the like and can contain catalytically active metals, metal oxides, metal ions, metal chelates or other compounds which are catalytically active forms of the above-mentioned metals. The perfluorinated polymer can be incorporated onto (or in) the support by a variety of methods such as coextrusion, melt decomposition, deposition as a thin film and the like, including the procedures of U.S. Pat. No. 4,303,551 and 4,791,081 incorporated by reference. Preferably, the support is porous alumina or silicon carbide.

A preferred embodiment of the perfluorinated polymers of the invention is directed to perfluorinated polymers prepared by polymerizing at least two monomers, one of which is ethylenically unsaturated and the other is represented by a perfluorinated monomer as disclosed in U.S. Pat. No. 4,330,654, incorporated by reference. For example the solid perfluorinated polymer catalyst contains a repeating structure selected from the group consisting of:

(a)
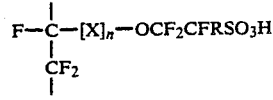

or (b)
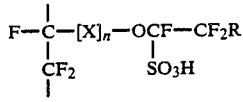

where n is 0, 1 or 2, R is a radical selected from the group consisting of fluorine and perfluoroalkyl radicals having from 1 to 10 carbon atoms; and X is selected from the group consisting of:

where m is an integer from 2 to 10 and Y is a radical selected from the class consisting of fluorine and the trifluoromethyl radical.

A preferred copolymer prepared by polymerizing perfluoroethylene with a perfluorovinyl ether containing attached sulfonic acid groups would have the following structure:

(c)
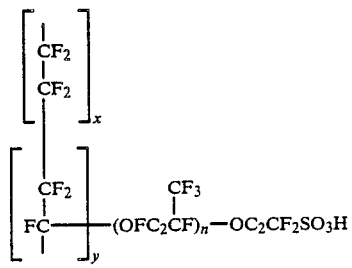

wherein n=1 or 2 and the ratio of x over y varies from about 2 to about 50. The polymer of structure (c) is available commercially under the trade-name of NAFION® resin. Catalysts of the above-noted structure (c) offer the advantages of high concentrations of accessible acidic groups in a solid phase.

The precise catalytic amount of the acidic perfluorinated polymer to be used will usually vary to some degree depending on the specific polymer, feed and conditions used for isomerization process. By way of illustration, the catalyst can be present from about 0.05 lbs per lb of feed per hour to about 10.0 lbs per lb of feed per hour and preferably from about 0.2 lbs to about 2 lbs per lb of feed per hour.

The isomerization is conducted in the presence of minor amounts of water which are usually present in the reaction solution at from about 1.5% to essentially anhydrous conditions based on the isomerization reaction solution. Somewhat higher amounts of water can be present but this could result in less desirable rate of reaction. Preferably, the water content of the reaction solution is from about 0.01% to about 0.7% based on the isomerization reaction solution.

The isomerization is usually conducted at moderately elevated temperatures. Suitable temperatures are from about 50° C. to about 180° C. at ambient to slightly elevated pressures. Preferably, the reaction temperature is from about 60° C. to about 150° C. at ambient to 10 psig pressure. The pressure of the process is not critical but is conveniently ambient to 10 psig, although use of higher pressures is not excluded.

Thus, the isomerization reaction is conducted by contacting a feed stream containing liquid by-products from the preparation of a bis-phenol, such as 2,4'-dihydroxy-2,2'-diphenyl propane and related by-products and optionally (phenol) washings from the crystallization of bis-phenol-A, or 2,4'-dihydroxy-9,9'-diphenylfluorene and related by-products from bisphenol-fluorene manufacture with the perfluorinated cationic exchange resin of the invention under moderately elevated temperatures. The feed stream passes through the resin catalyst for a period of time sufficient to effect isomerization depending on the feed rate, size of the resin bed, the particular resin used and the like as can readily be determined by those of skill in the art. The resulting isomerization product enriched in the desired bis-phenol, e.g., one having a desired 4,4'-dihydroxy form, such as bis-phenol-A, p,p'-bis-phenolfluorene or the like, is then recovered. Usually the recovered product is recycled back to a zone in which the bis-phenol is prepared by condensation of a ketone (acetone) and phenol.

The reaction time in the isomerization or in the condensation depends on the reaction temperature and other reaction conditions, including whether the process is continuous or batch processing.

Another embodiment of the present invention is directed to a process for the preparation of a bis-phenol which comprises (a) condensing a ketone, such as acetone, 9-fluorenone or the like, and a phenol in the presence of an acid, such as an acidic cation exchange resin, (b) purifying the product of (a) the desired bis-phenol, and (c) isomerizing the by-products of the condensation step (a) optionally with any wash liquids from the crystallization step (b) in the presence of an acidic perfluorinated cation exchange resin catalyst to obtain a product enriched in the desired bis-phenol for recovery or recycle to the condensation step (a).

The condensation of ketone and phenol can be conducted using cation exchange resin conventionally known in the art for the condensation of acetone and phenol. In general, these are often mercaptan modified resins of the type conventionally known in the art which include any compound which will react with the acidic groups of the cation exchange resin to introduce a mercapto substituent into the resin. The resins effectiveness as the (mercaptan modified) resin in the condensation step of the process of the invention is to some extent influenced by their exchange capacities such that the greater the exchange capacity then the more desirable the resin. Preferably, the cation exchange capacity is at least about 0.5 and, preferably, greater than 4.0 meq/g dry weight. Also, those cation exchange resins having bound cationic exchange groups of the stronger exchange potential acids are preferred for use in the (mercaptan modified) resin condensation step of the process of the present invention. Acidic cation exchange resins suitable (for optional modification with a mercapto modifying agent) for use in the condensation step of the process of the invention include sulfonated styrene-divinyl-benzene copolymers, sulfonated crosslined styrene polymers, phenol-formaldehyde-sulfonic acid resins, benzene-formaldehyde-sulfonic acid resins, perfluorinated sulfonic acid resins and the like. These include resins under such tradenames as Amberlites (Rohm and Haas Co.), DOWEX ® (Dow Chemical Co.), Permutit QH (Permutit CO.), Chempro (Chemical Process Co.), Lewatit (Bayer A. G.), NAFION and the like. Strong acid sulfonated styrene-divinylbenzene copolymer resins are preferred. Commercially available aromatic sulfonic acid resins are generally obtained as sodium salts and are converted to the acid form prior to use. Both modified macroreticular resins and microreticular resins are useful in the condensation process of the present invention. The choice of resin will of course depend on the starting materials, the reaction conditions and the effect of an individual resin under the conditions selected, which determination and selection is within the skill of the art. Suitable mercaptan modifying agents include simple alkyl mercaptans, alkyl mercapto amines, mercapto alcohols, and precursors and the like, for example, methyl mercaptan, propylaminopropyl mercaptan, mercaptan, bis-2-(mercaptoethyl)-amine, mercapto ethanol, thiazolidine and the like, although unmodified resins are also useful.

The condensation reaction conditions can vary. For convenience the reaction is usually conducted at moderately elevated temperature of from about 50° C. to about 130° C. at ambient pressures, although lower or higher temperatures and pressures are not excluded.

In the preparation of the bis-phenols, an excess of the phenol is usually desirable, generally from about 5 to about 20 moles of phenol per mole of ketone, is desirable for high conversion of the ketone. Inert solvents or diluents, although they could be used, are not necessary in either the preparation of the bis-phenol or in the isomerization of the undesired by-product except at low temperature.

The bis-phenol product, e.g., bis-phenol-A, bis-phenolfluorene or the like, is passed to a concentrator where the volatile ketone and excess phenol and water are removed as an overhead fraction. The crude bis-phenolfluorene product is then recrystallized from toluene to yield purified bis-phenolfluorene (about 90:8 ratio of p,p' to o,p' as determined by HPLC analysis). The mother liquid by-product stream from the crystallization zone is evaporated (to remove toluene) and the bottoms passed to the isomerization zone, combined with the phenol and isomerized in the presence of a perfluorinated cation exchange resin catalyst as described above. The product of this isomerization enriched in bis-phenolfluorene is recovered or preferably recycled to the condensation zone.

Other bis-phenol products can be recovered by conventional recovery techniques, including recrystallization, adduct formation and the like.

DETAILED DESCRIPTION OF THE DRAWING

Figure 1:
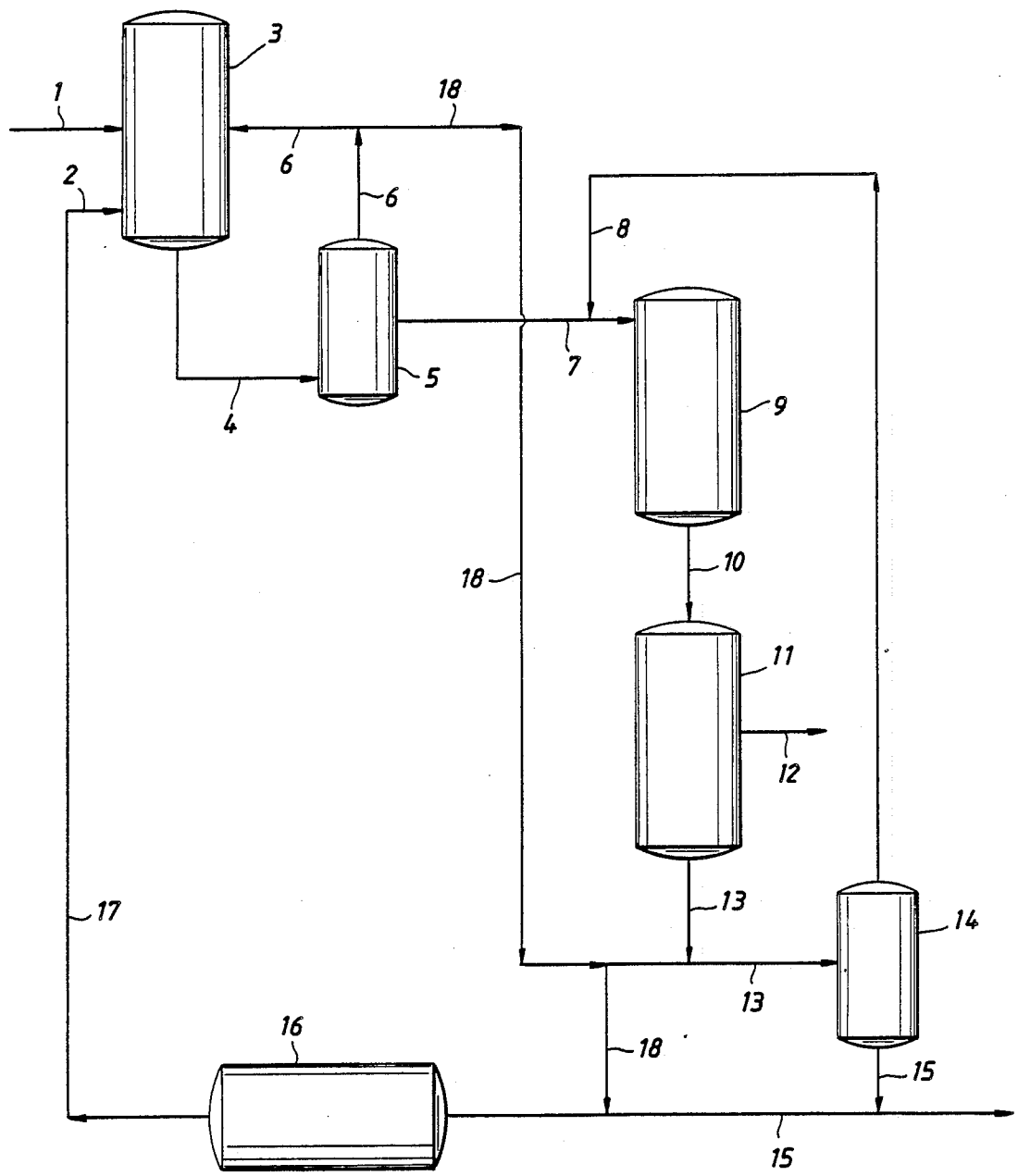
FIG. 1 is a schematic drawing of a process to prepare a bis-phenolfluorene in which 9-fluorenone and phenol are reacted to form a bis-phenolfluorene and the undesired by-product isomers are subsequently treated in the presence of a perfluorinated polymer and in which the preparation of bis-phenolfluorene takes place in the presence of a (mercaptan modified) resin cation exchange.

With reference to FIG. 1, 9-fluoreneone and phenol reactants are injected into a condensation reactor 3 via lines 1 and 2, along with any recycle isomerization product added via line 17. Any conventional condensation catalyst effective for the formation of a bis-phenol, e.g., bis-phenolfluorene, can be used. However, it is advantageous that the reactor contains an unmodified or modified cation exchange resin, such as a microreticular (gel) sulfonated polystyrene divinylbenzene acidic cation exchange resin at about 50° C. to 100° C. The bis-phenolfluorene reaction product is passed via line 4 into a concentrator 5 in which excess phenol and water are recovered for recycle via line 6 to zone 3 and crude bis-phenolfluorene product is recovered and passed via line 7 to purifier 9, e.g., crystallizer. A solvent such as toluene is added via line 8 to dissolve bis-phenolfluorene. The slurry is passed via line 10 into separator 11 wherein recrystallized bis-phenolfluorene is separated from the solvent and mother liquid and recovered via line 12 into a melter. The by-product solvent and mother liquid is removed from the separator 11, via line 13. The isomers diluted in recycled phenol are injected into line 13 and/or line 15 via line 18. The solvent is distilled in 14. The isomers are passed via line 15 into an isomerization zone 16. The isomerization zone is maintained at about 60°–90° C. and contains an acidic polymer which is used in a perfluorinated form. Some condensation may also occur at the same time because of the presence of unreacted 9-fluorenone in this recycle stream. The isomerization product which is increased in concentration of the desired bis-phenolfluorene is recovered or recycled to the condensation reactor via line 17.

While the invention has been illustrated with particular apparatus, those of skill in the art will appreciate that equivalent or analogous apparatus or parts thereof can be employed and that the use of equipment operated in series or in parallel can be used. Batch or continuous form can be used. The solid catalysts can be used as a slurry with the reactants in batch processing or in a fixed bed in a continuous process.

ILLUSTRATIVE EMBODIMENT

The invention is illustrated by the following embodiments which should not be regarded as limiting the invention in any way.

EMBODIMENT 1

Experiments were performed in batch using a 1:3 catalyst to reactant weight ratio for the following systems: (1) Dow XU-40036.01 perfluorocarbonsulfonic acid polymer on alumina-based porous support and (2) Dow XU-40036.02, perfluorocarbonsulfonic acid polymer on silicon carbide porous support as compared to (3) macroreticular DOWEX MSC-1 and (4) alpha-Alumina carrier alone. Each catalyst was pre-dried in vacuum oven at 60°–70° C. for 1–2 days and the feed bis-phenol obtained by the condensation of 9-fluorenone and phenol. The products were analyzed by high performance liquid chromatography (HPLC). The relative acid contents for the Dowex MSC-1, XU-40036.01 and XU-40036.02 catalysts are respectively 4.87, 0.14 and 0.22 mmoles/g (dry basis). Results of the experiments are given in Table 1 and illustrate that the desired isomerization of p,p'-bis-phenolfluorene to the o,p'-bis-phenolfluorene took place with the perfluorinated catalysts and better than macroreticular DOWEX MSC-1 cation exchange resin on a per meg H+ basis. Essentially no isomerization occurred using alpha-Alumina alone.

TABLE 1 p,p'-Bisphenolfluorene Isomerization to o,p'-Bisphenolfluorene
(Phenol: p,p'-BPFL = 85:15:Reactants: Catalyst = 3:1)

| Catalyst | Temperature (°C.) | Reaction Time, Hr | % Normalized Area[a] | | | | p,p'-o,p'/ Dimer | p,p'/ Trimer |
|---|---|---|---|---|---|---|---|---|
| | | | p,p'-BPFL | o,p'-BPFL | Trimer | Others | | |
| DOW XU - 40036.01[b] | 80 | 0 | 98.73 | 0.63 | 0.12 | 0.52 | 156.7 | 822.8 |
| | | 24 | 95.25 | 3.23 | 0.37 | 1.14 | 29.5 | 257.4 |
| | 120 | Initial | 97.59 | 1.48 | 0.27 | 0.66 | 65.9 | 361.4 |
| | | 23 | 75.58 | 8.93 | 1.15 | 14.24 | 8.5 | 65.7 |
| DOW XU - 40036.02[c] | 80 | 0 | 98.73 | 0.63 | 0.12 | 0.52 | 156.7 | 822.8 |
| | | 24 | 93.03 | 4.66 | 0.64 | 1.68 | 20.0 | 145.4 |
| DOWEX MSC-1 | 70 | Initial | 97.97 | 0.60 | 0.16 | 1.28 | 163.3 | 612.3 |
| (0.17% w H2O) | | 24.25 | 92.03 | 5.32 | 0.80 | 1.84 | 17.3 | 115.0 |
| (0.22% w H2O) | 85 | Initial | 97.97 | 0.60 | 0.16 | 1.28 | 163.3 | 612.3 |
| | | 24.75 | 87.46 | 6.59 | 0.98 | 4.97 | 13.3 | 89.2 |
| alpha-Alumina[d] | 12 | Initial | 97.61 | 1.49 | 0.22 | 0.68 | 65.5 | 443.7 |
| | | 23.5 | 97.08 | 1.57 | 0.42 | 0.93 | 61.8 | 231.1 |

[a]HPLC area as detected under 280 nm.
[b]Fifteen percent fluorocarbonsulfonic acid polymer coated on 85% alumina-based porous support, 0.14 meq/g acid capacity (dry).
[c]Ten percent fluorcarbonsulfonic acid polymer coated on 90% silicon carbide-based porous support, 0.22 meq/g acid capacity (dry).
[d]Shell 1048-115-14 alpha-Alumina carrier; porosity: 0.361; surface area: 0.34 $m^2/g$.

Embodiment 2

Following procedures similar to those described in Embodiment 1, by-products from the preparation of p,p'-bis-phenolfluorene comprising o,p'-bis-phenolfluorene, p,p'-dimer, trimers and other by-products are isomerized under similar conditions in a continuous manner with simultaneous conversion of any 9-fluorenone in the by-products.

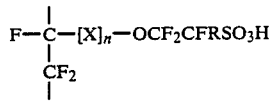

(a)

or

TABLE 2

Continuous o,p-bisphenolfluorenone Isomerization to p,p'-bisphenolfluorene with
Simultaneous 9-fluorenone Conversion
15% fluorocarbon sulfonic acid polymer coated on 85% alumina-based porous support

| Reactor Temperature (°C.) | 1/WHSV,[b] hr | % W Feed Composition | | | | | Results[a] | | |
|---|---|---|---|---|---|---|---|---|---|
| | | H2O | p,p'-BPFL | Phenol | 9-Fluorenone | Others | % W H2O | 9-Fluorenone % Conversion | % p,p'-BPFL Formed[c] |
| 92.6–105 | 1.03 | 0.07 | 11.53 | 85.07 | 1.71 | 1.26 | 0.43 | 60.6 | 115.2 |
| 92.6–105 | 0.47 | 0.06 | 9.94 | 83.98 | 2.25 | 3.52 | 0.32 | 48.5 | 106.0 |
| 120.9–135 | 0.45 | 0.06 | 13.09 | 82.39 | 1.03 | 3.06 | 0.43 | 76.5 | 121.3 |
| 121.2–135 | 0.68 | 0.06 | 14.67 | 83.64 | 0.69 | 0.55 | 0.46 | 84.2 | 134.6 |
| 121.6–135 | 0.82 | 0.07 | 15.25 | 83.33 | 0.57 | 0.35 | 0.50 | 86.9 | 139.2 |
| 92.6–105 | 0.64 | 0.25 | 8.53 | 85.89 | 2.95 | 2.19 | 0.25 | 32.4 | 105.2 |
| 92.6–105 | 0.83 | 0.29 | 8.70 | 86.70 | 2.96 | 1.22 | 0.29 | 32.0 | 113.4 |
| 121.2–135 | 0.81 | 0.27 | 13.26 | 84.54 | 1.34 | 0127 | 0.27 | 69.3 | 132.6 |
| 121.2–135 | 0.46 | 0.27 | 11.42 | 85.07 | 1.97 | 1.04 | 0.27 | 54.9 | 124.1 |

[a]HPLC area as detected under 280 nm.
[b]WHSV is weight hourly space velocity.
[c]% p,p'-BPFL is computed from 9-Fl conversion. Numbers exceeding 100% indicate p,p'-BPFL is formed from isomerization of o,p-BPFL and trimer into p,p'-BPFL.

What is claimed is:

1. A process for isomerizing by-products from the preparation of a desired bisphenolfluorene, which process comprises treating said byproducts with a catalytic amount of an acidic perfluorinated polymer at about 50° C. to about 150° C. and at about ambient to about 10 psig pressure to isomerize said byproducts to a desired bisphenolfluorene.

2. The process according to claim 1 wherein the perfluorinated polymer is a copolymer of an ethylenically unsaturated monomer and a perfluorinated monomer containing acid or precursor acid groups.

3. The process according to claim 2 wherein the polymer contains from about 0.5 to about 50 moles percent of perfluorinated sulfonic acid groups.

4. The process according to claim 3 wherein the perfluorinated polymer contains a repeating structure selected from the group consisting of:

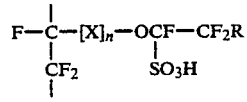

(b)

where n is 0, 1 or 2; R is a radical selected from the group consisting of fluorine and perfluoroalkyl radicals having from 1 to 10 carbon atoms; and X is selected from the group consisting of:

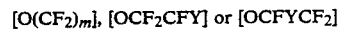

where m is an integer from 2 to 10 and Y is a radical selected from the class consisting of fluorine and the trifluoromethyl radical.

5. A process according to claim 9 wherein the polymer is prepared by polymerizing perfluoroethylene with a perfluorovinyl ether containing sulfonic acid groups and has the structure

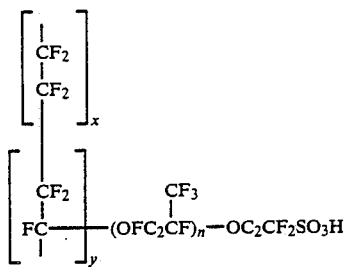

wherein n is 1 or 2 and the ratio of x over y is from about 2 to about 50.

6. The process according to claim 1 wherein the polymer is used with a solid support.

7. The process according to claim 6 wherein the support is porous alumina or silicon carbide.

8. The process according to claim 1 wherein the polymer is a copolymer of an ethylenically unsaturated monomer and a perfluorinated monomer containing sulfonic acid groups.

9. The process according to claim 8 wherein the polymer is used with a solid support.

10. A process for the preparation of a bis-phenolfluorene which comprises (a) condensing 9-fluorenone and a phenol in the presence of an acidic cation exchange resin, (b) purifying the product of (a) to obtain the desired bis-phenolfluorene, and (c) isomerizing the by-products of step (a) at about 50° C. to about 150° C. and at about ambient to about 10 psig pressure in the presence of an acidic perfluorinated polymer to obtain a product enriched in the desired bis-phenofluorene for recovery or recycle to the condensation step (a).

11. The process according to claim 10 wherein the perfluorinated polymer is a copolymer of an ethylenically unsaturated monomer and/or perfluorinated monomer containing acid or precursor acid groups.

12. The process according to claim 11 wherein the polymer contains from about 0.5 to about 50 mole percent of perfluorinated sulfonic acid groups.

13. The process according to claim 12 wherein the perfluorinated polymer contains a repeating structure selected from the group consisting of:

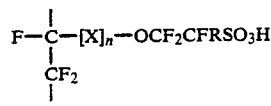

or

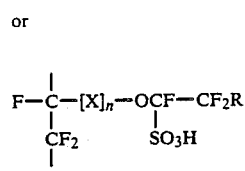

where n is 0, 1 or 2; R is a radical selected from the group consisting of fluorine and perfluoroalkyl radicals having from 1 to 10 carbon atoms; and X is selected from the group consisting of:

$[O(CF_2)_m]$, $[OCF_2CFY]$ or $[OCFYCF_2]$ where m is an integer from 2 to 10 and Y is a radical selected from the class consisting of fluorine and the trifluoromethyl radical.

14. A process according to claim 8 wherein the polymer is prepared by polymerizing perfluoroethylene with a perfluorovinyl ether containing sulfonic acid groups and has the structure

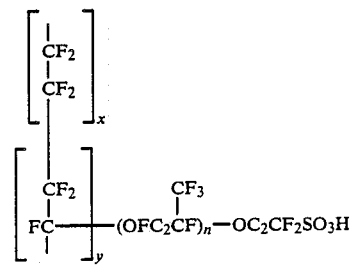

15. The process according to claim 10 wherein the polymer is used with a solid support.

16. The process according to claim 15 wherein the support is porous alumina or silicon carbide.

17. The process according to claim 10 wherein the polymer is a copolymer of an ethylenically unsaturated monomer and a perfluorinated monomer containing sulfonic acid groups.

18. The process according to claim 17 wherein the polymer is used with a solid support.

19. A process according to claim 10 wherein the resin in the condensation step (a) is an unmodified resin.

20. A process according to claim 10 wherein the resin in the condensation step (a) is a modified resin.

* * * * *